United States Patent [19]

Schmidt et al.

[11] Patent Number: 4,783,575

[45] Date of Patent: Nov. 8, 1988

[54] ISOMERIZATION WITH CYCLIC HYDROCARBON CONVERSION

[75] Inventors: Robert J. Schmidt, Rolling Meadows; Laurence O. Stine, Western Springs, both of Ill.

[73] Assignee: UOP Inc., Des Plaines, Ill.

[21] Appl. No.: 134,622

[22] Filed: Dec. 17, 1987

[51] Int. Cl.$^4$ ............................................. C07C 5/13
[52] U.S. Cl. .................................. 585/748; 585/752; 585/940
[58] Field of Search .................... 585/940, 748, 752

[56] References Cited

U.S. PATENT DOCUMENTS

| | | | |
|---|---|---|---|
| 2,915,571 | 12/1959 | Haensel | 260/683.68 |
| 3,242,228 | 3/1966 | Riordan et al. | 585/748 |
| 3,449,264 | 6/1969 | Myers | 585/748 |
| 3,457,162 | 7/1969 | Riedl et al. | 585/940 |
| 3,631,117 | 12/1971 | Kovach et al. | 260/666 |

FOREIGN PATENT DOCUMENTS 716555  8/1965  Canada ................................ 585/940

*Primary Examiner*—Curtis R. Davis
*Attorney, Agent, or Firm*—Thomas K. McBride; John G. Tolomei

[57] ABSTRACT

A $C_4$–$C_6$ feed to an isomerization zone containing substantial amounts of cyclic hydrocarbons is contacted with a high chloride, platinum alumina catalyst to simultaneously open cyclic hydrocarbon rings and isomerize paraffins to more highly branched paraffins. The process can operate at relatively low severity conditions that provide favorable equilibrium conditions for isoparaffin conversion. The ring opening is also obtained without excessive generation of light hydrocarbons. Multiple stage reaction zones may be used to operate the first stage at slightly higher severity than the second stage to maximize ring opening and obtain favorable equilibrium of iso to normal paraffins.

6 Claims, 2 Drawing Sheets

ISOMERIZATION WITH CYCLIC HYDROCARBON CONVERSION

BACKGROUND OF THE INVENTION

This invention relates generally to the isomerization of hydrocarbons. This invention relates more specifically to the isomerization of light paraffins and the opening of cyclic hydrocarbon rings.

DESCRIPTION OF THE PRIOR ART

High octane gasoline is required for modern gasoline engines. Formerly it was common to accomplish octane number improvement by the use of various lead-containing additives. As lead is phased out of gasoline for environmental reasons, it has become increasingly necessary to rearrange the structure of the hydrocarbons used in gasoline blending in order to achieve high octane ratings. Catalytic reforming and catalytic isomerization are two widely used processes for this upgrading.

A gasoline blending pool normally includes $C_4$ and heavier hydrocarbons having boiling points of less than 205° C. (395° F.) at atmospheric pressure. This range of hydrocarbon includes $C_4$–$C_6$ paraffins and especially the $C_5$ and $C_6$ normal paraffins which have relatively low octane numbers. The $C_4$–$C_6$ hydrocarbons have the greatest susceptibility to octane improvement by lead addition and were formerly upgraded in this manner. Octane improvement can also be obtained by catalytically isomerizing the paraffinic hydrocarbons to rearrange the structure of the paraffinic hydrocarbons into branch-chained paraffins or reforming to convert the $C_6$ and heavier hydrocarbons to aromatic compounds. Normal $C_5$ hydrocarbons are not readily converted into aromatics, therefore, the common practice has been to isomerize these lighter hydrocarbons into corresponding branch-chained isoparaffins. Although the $C_6$ and heavier hydrocarbons can be upgraded into aromatics through hydrocyclization, the conversion of $C_6$'s to aromatics creates higher density species and increases gas yields with both effects leading to a reduction in liquid volume yields. Therefore, it is common practice to charge the $C_6$ paraffins to an isomerization unit to obtain $C_6$ isoparaffin hydrocarbons. Consequently, octane upgrading commonly uses isomerization to convert $C_6$ and lighter boiling hydrocarbons and reforming to convert $C_7$ and higher boiling hydrocarbons. Converting $C_6$ to cyclic hydrocarbons to isoparaffins instead of aromatics can also improve overall octane ratings. Octane ratings in the U.S. and elsewhere represent a blend of research and motor octane values. The difference, sometimes referred to as octane sensitivity, between motor and research octane values is high for aromatics and $C_6$ cyclics with motor octane trailing research values by as much as 10 numbers. On the other hand, the octane sensitivity for isohexanes varies by no more than a few numbers. The relatively higher motor octane number and reduced octane sensitivity again favors the conversion of $C_6$ cyclic paraffins to isoparaffins.

The isomerization of paraffins is a reversible first order reaction. The reaction is limited by thermodynamic equilibrium. The basic types of catalyst systems that are used in effecting the reaction are a hydrochloric acid promoted aluminum chloride system and a supported aluminum chloride catalyst. Either catalyst is very reactive and can generate undesirable side reactions such as disproportionation and cracking. These side reactions not only decrease the product yield but can form olefinic fragments that combine with the catalyst and shorten its life. One commonly practiced method of controlling these undesired reactions has been to carry out the reaction in the presence of hydrogen.

A large percentage of the $C_4$–$C_6$ paraffin fractions that are available as feedstocks for $C_4$–$C_6$ isomerization processes include cyclic hydrocarbons. These cyclic hydrocarbons tend to be absorbed on the isomerization catalysts. Absorption of the cyclic compounds blocks active sites on the catalyst and thereby excludes the isomerizable paraffins from the catalyst. This exclusion diminishes the overall conversion of the process. As a result, removal of cyclic hydrocarbons from an isomerization process will increase conversion of the paraffins to more highly branched paraffins and rearrangement of the cyclic hydrocarbons to branched paraffins will increase volume yield. Complete removal of cyclic hydrocarbons by ordinary separation cannot be achieved due to the boiling points of the $C_6$ paraffins and many of the cyclic hydrocarbons, in particular, normal hexane and methylcyclopentane.

U.S. Pat. No. 2,915,571 teaches the reduction of naphthenes in an isomerization feed fraction by contact with a ring opening catalyst containing an iron group metal in a first reaction zone, and subsequent isomerization of the feed fraction by contact with a different catalyst in an isomerization zone. Opening of the cyclic hydrocarbons has the two fold advantage of eliminating the cyclic hydrocarbons that can cause catalyst fouling and increasing the volume of lower density isomerizable hydrocarbons that in turn increases product yields. The use of different catalysts for ring opening and isomerization imposes a major drawback on the process of U.S. Pat. No. 2,915,571 since it requires at least one additional reaction zone. U.S. Pat. No. 3,631,117 describes a process for the hydroisomerization of cyclic hydrocarbons that uses a zeolite supported Group VII metal as a ring opening catalyst at high severity conditions and as an isomerization catalyst at low severity conditions to obtain cyclic isomers having at least one less carbon atom per ring than the unconverted cyclic hydrocarbons. When high severity operating conditions are used to open rings, substantial cracking of $C_4$–$C_6$ hydrocarbons to light ends will also occur. Therefore, high severity conditions to open rings in $C_4$–$C_6$ hydrocarbon feedstocks are usually avoided.

The disadvantages of dual catalyst systems, additional reaction zones and production of light ends have provided substantial obstacles to the conversion of cyclic hydrocarbons contained in feedstocks of isomerizable $C_4$–$C_6$ hydrocarbons.

It has now been discovered that cyclic hydrocarbons can be converted to branched chain isomers in a paraffin isomerization process using a single catalyst system, at low severity conditions.

Accordingly, it is an object of this invention to increase the activity of the catalyst in a paraffin isomerization process.

It is a further object of this invention to increase the yield of $C_4$–$C_6$ branched chain paraffins in a paraffin isomerization process.

Another object of this invention is the cleavage of cyclic hydrocarbons and conversion to branch chain paraffins without reducing the carbon atoms in the resulting paraffins.

Yet another object of this invention is to improve the motor octane number of cyclohexanes.

A yet further object of this invention is the isomerization of $C_4$–$C_6$ paraffins and the conversion of cyclic hydrocarbons to branch paraffins with a single catalyst system.

BRIEF DESCRIPTION OF THE INVENTION

Figure 1:
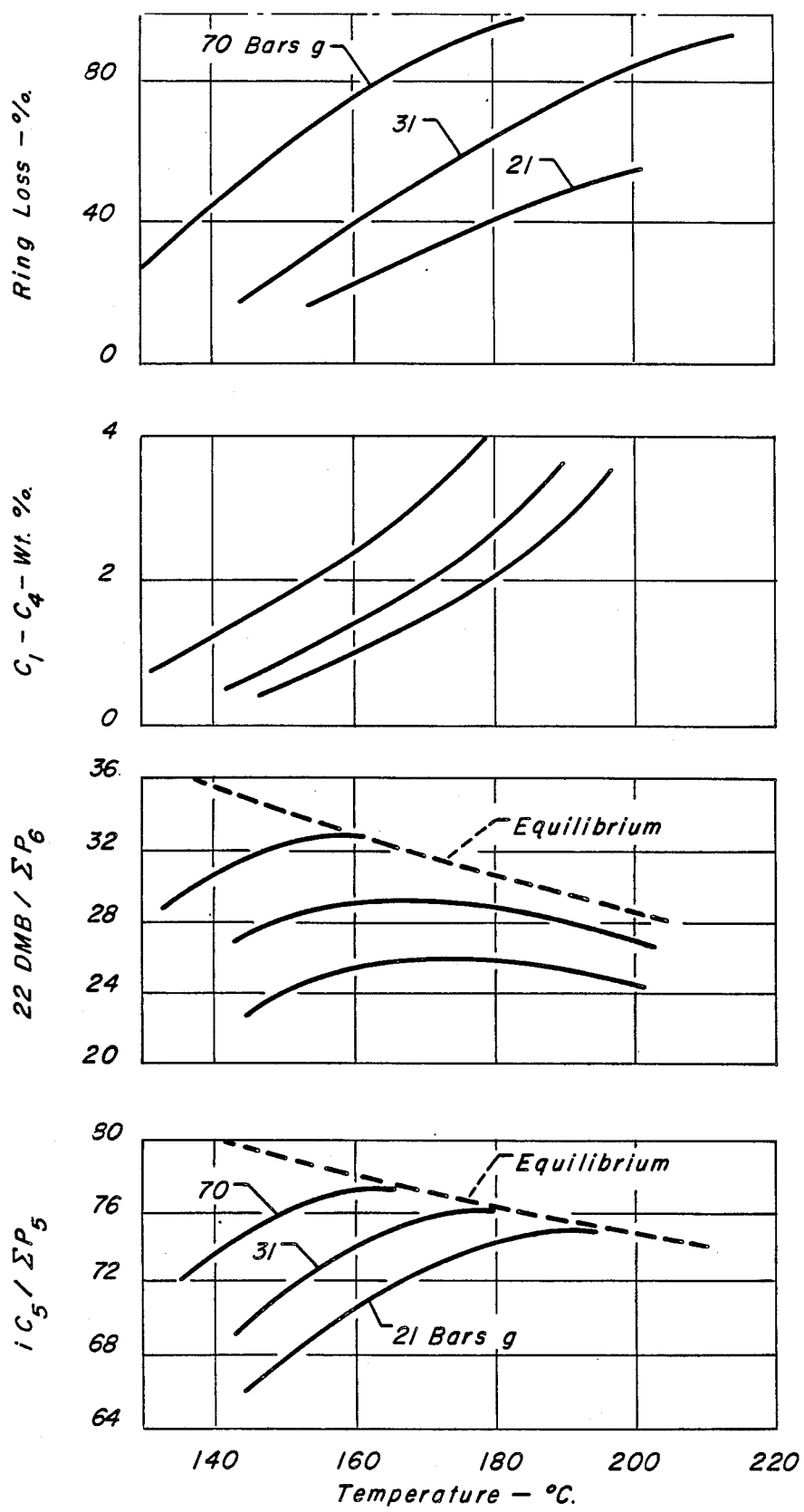
FIGS. 1 and 2 are graphs of performance parameters for the process of this invention plotted as a function of temperature.

This invention is a process for isomerizing a feedstock comprising normal paraffins having 4–6 carbon atoms and at least 2 wt.% of cyclic hydrocarbons that achieves high conversion and good stability by opening the rings of the cyclic hydrocarbons without appreciable chain shortening. The invention uses a highly active chlorided platinum/aluminum catalyst in the isomerization reaction which has been discovered to selectively open the rings of cyclic hydrocarbons at temperatures at or slightly greater than typical isomerization temperatures without generating light gases by subsequent cracking of opened rings. Eliminating the cyclic hydrocarbons by ring cleavage offers the dual advantages of increasing the activity and stability of the catalyst while also raising the liquid volume yields.

Thus, in one embodiment this invention is a process for the isomerization of a feedstream comprising $C_4$–$C_6$ isomerizable hydrocarbons and including at least 2 wt.% cyclic hydrocarbons. The process comprises passing a feedstream to a reaction zone and contacting the feedstream with a catalyst comprising alumina, from 0.1 to 0.25 wt.% platinum, and from 2 to 10 wt.% of a chloride component at isomerization conditions including a temperature in the range of from 40°–260° C. (105°–500° F.), a pressure of from 7 to 70 barsg and a space velocity of from 0.5 to 12 while maintaining a chloride concentration of from 30–300 ppm in the reaction zone. An effluent is recovered from the reaction zone having a wt.% concentration of cyclic hydrocarbons at least 40% lower than the feedstream.

In another embodiment this invention is a process for the isomerization of a feedstream comprising $C_4$–$C_6$ isomerizable hydrocarbons and including at least 2 wt.% cyclic hydrocarbons. The process comprises passing a feedstream to a first reaction zone and contacting the feedstream with a catalyst comprising alumina, from 0.1 to 0.25 wt.% platinum, and from 2 to 10 wt.% of a chloride component at isomerization conditions including a temperature in the range of from 100°–260° C. (160°–500° F.), a pressure of from 7 to 70 barsg and a space velocity of from 0.5 to 12 while maintaining a chloride concentration of from 30 to 300 ppm in the reaction zone. An effluent having a reduced concentration of cyclic hydrocarbons is recovered from the first reaction zone and passed to a second reaction zone where the feedstream contacts a catalyst having the same composition as that used in the first reaction zone at isomerization conditions including a temperature in the range of from 40°–200° C. (105°–390° F.), a pressure of from 7 to 70 barsg, and a space velocity of from 0.1 to 10 while maintaining a chloride concentration of from 30 to 300 ppm in the second reaction zone. An effluent having a wt.% concentration of cyclic hydrocarbons at least 40% lower than said feedstream is recovered from the second reaction zone.

Other aspects of this invention relate to feedstream compositions, processing conditions, reaction zone arrangements and catalyst details.

DETAILED DESCRIPTION OF THE INVENTION

The feedstocks that can be used in this invention include hydrocarbon fractions rich in $C_4$–$C_6$ normal paraffins. The term "rich" is defined to mean a stream having more than 50% of the mentioned component. In addition the feedstock will include cyclic hydrocarbons. In order to realize the advantages of this invention, the concentration of cyclics in the feedstock will at least equal that which would reduce the activity of an isomerization catalyst by adsorption of the cyclics thereon or which, due to its higher density in contrast to branched chain paraffins, would represent a significant loss of liquid volume yield. Normally, the minimum concentration is 2 wt.%. There is no upper limit on the concentration of cyclic hydrocarbons in the feed since the process of this invention can be used to process feedstocks composed primarily of cyclic hydrocarbons. However, the feedstocks will usually contain from 2 to 30 wt.% of cyclic hydrocarbons. Possible types of cyclic hydrocarbons in the feed include alicyclic and aromatic hydrocarbons. If unsaturated cyclic hydrocarbons including benzene or benzene derivatives enter the process, they are rapidly saturated therein and effectively serve as additional cycloalkane components. Typically, the cyclic components will have between 5 to 7 carbon atoms. The feed components will usually comprise $C_4$–$C_7$ cyclic and paraffinic hydrocarbons with n-hexane and n-pentane providing most of the paraffinic components. Useful feedstocks that will contain cyclic components include light natural gasoline, light straight run naphtha, gas oil condensate, light raffinates, light reformate, light hydrocrackate, field butanes, and straight run distillates having distillation end point of about 77° C. (170° F.) and containing substantial quantities of $C_4$–$C_6$ paraffins. As mentioned, the feedstream may also contain low concentrations of unsaturated hydrocarbons such as benzene or other olefins as well as hydrocarbons having more than 6 carbon atoms. The concentration of these materials should be limited to 10 wt.% for unsaturated compounds and 20 wt.% for heavier hydrocarbons in order to restrict hydrogen consumption and cracking reactions.

Hydrogen is admixed with the feed in an amount that will provide a hydrogen to hydrocarbon molar ratio of from 0.01 to 10 in the effluent from the isomerization zone. Preferably, the hydrogen to hydrocarbon ratio is in the range of 0.05 to 5. Although no net hydrogen is consumed in the isomerization reaction, the isomerization zone will have a net consumption of hydrogen often referred to as the stoichiometric hydrogen requirement which is associated with a number of side reactions that occur. These side reactions include saturation of olefins and aromatics, cracking and disproportionation. For feeds having a high level of unsaturates, satisfying the stoichiometric hydrogen will require a higher hydrogen to hydrocarbon ratio for the feed at the inlet of the isomerization zone. Hydrogen in excess of the stoichiometric amounts for the side reactions is maintained in the reaction zone to provide good stability and conversion by compensating for variations in feedstream compositions that alter the stoichiometric hydrogen requirements and to prolong catalyst life by suppressing side reactions such as cracking and disproportionation. If left unchecked, the side reactions reduce conversion and lead to the formation of carbonaceous compounds, usually referred to as coke, that foul the catalyst.

When the hydrogen to hydrocarbon ratio exceeds 0.05, it is not economically desirable to operate the isomerization process without the recycle of hydrogen to the isomerization zone. Thus, recovery facilities for hydrogen from the effluent will be provided. Hydrogen may be added to the feed mixture in any manner that provides the necessary control for the addition of the hydrogen quantities.

The hydrogen and hydrocarbon feed mixture is contacted in the reaction zone with an isomerization catalyst. The isomerization catalyst consists of a high chloride catalyst on an aluminum base containing platinum. The aluminum is preferably an anhydrous gamma-alumina with a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt.% of the platinum. Other platinum group metals may be present in a concentration of from 0.1 to 0.25 wt.%. The platinum component may exist within the final catalytic composite as an oxide or halide or as an elemental metal. The presence of the platinum component in its reduced state has been found most suitable for this process.

The catalyst also contains a chloride component. The chloride component termed in the art "a combined chloride" is present in an amount from about 2 to about 10 wt.% based upon the dry support material. The use of chloride in amounts greater than 5 wt.% have been found to be the most beneficial for this process.

There are a variety of ways for preparing the catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of the chloride must be incorporated into the catalyst by the addition or formation of aluminum chloride to or on the platinum-aluminum catalyst base. An alternate method of increasing the chloride concentration in the final catalyst composite is to use an aluminum hydrosol to form the aluminum carrier material such that the carrier material also contains at least a portion of the chloride. Halogen may also be added to the carrier material by contacting the calcined carrier material with an aqueous solution of the halogen acid such as hydrogen chloride.

It is generally known that high chlorided platinum-alumina catalysts of this type are highly sensitive to sulfur and oxygen-containing compounds. Therefore, the feedstock must be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$-$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feedstream by hydrotreating. A variety of commercial dryers are available to remove water from the feed components. Adsorption processes for the removal of sulfur and water from hydrocarbon streams are also well known to those skilled in the art.

In this invention, it is also recognized that cyclic hydrocarbons, especially $C_6$ cyclics such as benzene, cyclohexane and methylcyclopentane adversely affect the degree of paraffin isomerization. The adverse effect is believed to be caused by preferential adsorption of the cyclic hydrocarbons on the catalyst surface and the resulting exclusion of the paraffinic hydrocarbons. The process of this invention uses the aforementioned catalyst at selected operating conditions to eliminate the cyclics by their contact therewith while converting the cyclics to provide addtitional isomerization product. It is not necessary to achieve a complete elimination of the rings in order to enjoy the benefits of this invention. Conversion of only a small wt.% of the rings in the entering feed will provide a substantial increase in the isoparaffin yield. Generally, the process will be operated to open at least 40 wt.% of the rings in the entering feed. When the cyclic hydrocarbon concentration of the feed exceeds 15 wt.%, a greater degree of ring opening may be sought such that the cyclic hydrocarbon concentration in the effluent from the reaction zone is kept below 7 wt.%. Temperature and pressure conditions directly affect the degree of ring opening.

Operating conditions within the isomerization zone are selected to maximize the production of isoalkane product from the feed components. Temperatures within the reaction zone will usually range from about 40°-260° C. (105°-500° F.). Lower reaction temperatures are preferred for purposes of isomerization conversion since they favor isoalkanes over normal alkanes in equilibrium mixtures. However, maximizing ring opening sometimes requires temperatures in excess of those that are most favorable from an equilibrium standpoint. For example, when the feed mixture is primarily $C_5$ and $C_6$ alkanes, temperatures in the range of 60° to 160° C. are desired from a normal-isoalkane equilibrium standpoint but, due to ring opening considerations, the preferred temperature range for this invention lies between 100°-200° C. When it is desired to also isomerize significant amounts of $C_4$ hydrocarbons, higher reaction temperatures are required to maintain catalyst activity. Thus, when the feed mixture contains significant portions of $C_4$-$C_6$ alkanes the most suitable operating temperatures for ring opening and isoalkane equilibrium coincide and are in the range from 145° to 225° C. The reaction zone may be maintained over a wide range of pressures. Pressure conditions in the isomerization of $C_4$-$C_6$ paraffins range from 7 barsg to 70 barsg. Higher pressures favor ring opening, therefore, the preferred pressures for this process are in the range of from 25 barsg to 60 barsg. The feed rate to the reaction zone can also vary over a wide range. These conditions include liquid hourly space velocities ranging from 0.5 to 12 hr.$^{-1}$, however, space velocities between 0.5 and 3 hr.$^{-1}$ are preferred.

Operation of the reaction zone also requires the presence of a small amount of an organic chloride promoter. The organic chloride promoter serves to maintain a high level of active chloride on the catalyst as small amounts of chloride are continuously stripped off the catalyst by the hydrocarbon feed. The concentration of promoter in the reaction zone is maintained at from 30 to 300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which may convert, in part, to hydrogen chloride. As long as the process streams are kept dry, there will be no adverse effect from the presence of small amounts of hydrogen chloride.

A preferred manner of operating the process is in a two-reactor or reaction zone system. The catalyst used in the process can be distributed equally or in varying proportions between the two reactors. The use of two reaction zones permits a variation in the operating conditions between the two reaction zones to enhance cyclic hydrocarbon conversion in one reaction zone and normal paraffin isomerization in the other. In this manner, the first reaction zone operates at higher temperature and pressure conditions that favor ring opening and performs only a portion of the normal to isoparaffin conversion. The likelihood of exothermic reactions, such as the hydrogenation of unsaturates, occurring in the initial portion of the reaction zone facilitates the use of higher temperatures therein. Once the rings have been opened by initial contact with the catalyst, the final reactor stage may operate at temperature conditions that are more favorable for isoalkane equilibrium.

Another benefit of using two reactors is that it allows partial replacement of the catalyst system without taking the isomerization unit off stream. For short periods of time, during which the replacement of catalyst may be necessary, the entire flow of reactants may be processed through only one reaction vessel while catalyst is replaced in the other.

Whether operated with one or two reaction zones, the effluent of the process will enter separation facilities in the recovery of an isoalkane product. At minimum, the separation facilities divide the reaction zone effluent into a product stream comprising $C_4$ and heavier hydrocarbons and a gas stream which is made up of lighter hydrocarbons and hydrogen. Suitable designs for rectification columns and separator vessels are well known to those skilled in the art. The separation section may also include facilities for recovery of normal isoalkanes. Normal isoalkanes recovered from the separation facilities may be recycled to the isomerization reaction zone to increase the conversion of normal alkanes to isoalkanes. Typical separation facilities will comprise a stabilizer section that receives the effluent from the reaction and includes at least one stabilizer column. The stabilizer column is operated to deliver a bottoms fraction containing $C_4$ and heavier hydrocarbons and an overhead fraction of $C_3$ hydrocarbons and lighter boiling compounds. The heavier hydrocarbons recovered from the bottom of the stabilizer column are cooled and may be further separated into a product stream and a reflux stream. $C_3$ and lighter hydrocarbons taken overhead from the stabilizer column are cooled, condensed and separated into a reflux stream that is returned to the process and a net gas stream. The net gas stream enters a scrubber section that contacts the gas with a suitable treatment solution for neutralizing and/or removing acidic components that may have originated with the chloride addition to the isomerization zone and may be present in the gas stream.

EXAMPLES

The process of this invention is characterized by substantial ring opening, high conversion, high selectivity and low production of $C_3$ and lighter gases as can be seen from the following examples. In these examples, the reactions were carried out in the presence of an alumina catalyst having 0.25 wt.% platinum and 5.5 wt.% chlorine which was prepared by vacuum impregnating an alumina base in a solution of chloroplatinic acid, 2% hydrochloric acid, and 3.5% nitric acid in a volume ratio of 9 parts solution to 10 parts base to obtain a peptized base material having a platinum to base ratio of approximately 0.9. The resulting mixture was cold-rolled for approximately 1 hour and evaporated until dry. Afterward, the catalyst was oxidized and the chloride content adjusted by contact with a 1M hydrochloric acid solution at 525° C. at a rate of 45 cc/hour for 2 hours. The catalyst was then reduced in electrolytic hydrogen at 565° C. for 1 hour and was found to contain approximately 0.25 wt.% Pt and approximately 1 wt.% chloride. Impregnation of active chloride to a level of approximately 5.5 wt.% was accomplished by sublimating aluminum chloride with hydrogen and contacting the catalyst with the sublimated aluminum chloride for approximately 45 minutes at 550° C.

EXAMPLE 1

A synthetic feedstock having the composition given in Table 1 was prepared. The feedstock was passed through a single reaction zone containing the previously described catalyst at a liquid hourly space velocity of 2 and a hydrogen to hydrocarbon molar ratio of 2. For a first series of runs the pressure was maintained at 21 barsg while the temperature was periodically increased over the range of about 140°-200° C. This procedure was repeated at pressures of 31 barsg and 70 barsg. The reaction zone effluent of each run was analyzed to determine the percentage of ring opening, the isopentane to $C_5$ hydrocarbon ratio, the 2,2-dimethylbutane to $C_6$ hydrocarbon ratio and the concentration of $C_1$-$C_4$ hydrocarbons contained therein.

These various properties were plotted as a function of temperature at the three different pressure levels and are shown in FIG. 1. Looking first at the plot for ring opening, the process of this invention provides a high degree of ring opening. Ring openings in excess of 40 percent were achieved at pressures as low as 21 bars for a temperature of 180° C. and temperatures as low as 135° C. for a pressure of 70 barsg. As the plot of $C_1$-$C_4$ hydrocarbon concentration shows only a small concentration of light materials was generated by the ring opening and isomerization reactions. Higher temperatures and pressures promoted additional cracking to lighter hydrocarbons; however, even at 70 barsg and 180° C., which conditions provided the highest ring opening, and are well above the conditions at which the process would normally be operated, the effluent concentration of $C_1$-$C_4$ hydrocarbons did not exceed 4 wt.%. The remaining two plots demonstrate the overall ability of the process to achieve a high conversion of $C_5$ and $C_6$ cyclic hydrocarbons to corresponding isoparaffins.

TABLE 1

| TYPICAL FEEDSTOCK, WT. % | |
|---|---|
| i-$C_5$ | 0 |
| n-$C_5$ | 44.0 |
| i-$C_6$ | 0 |
| n-$C_6$ | 45.6 |
| MCP | 4.0 |
| CH | 4.4 |
| BZ | 2.0 |
| $C_7+$ | 0 |
| Total | 100.0 |

EXAMPLE 2

Figure 2:
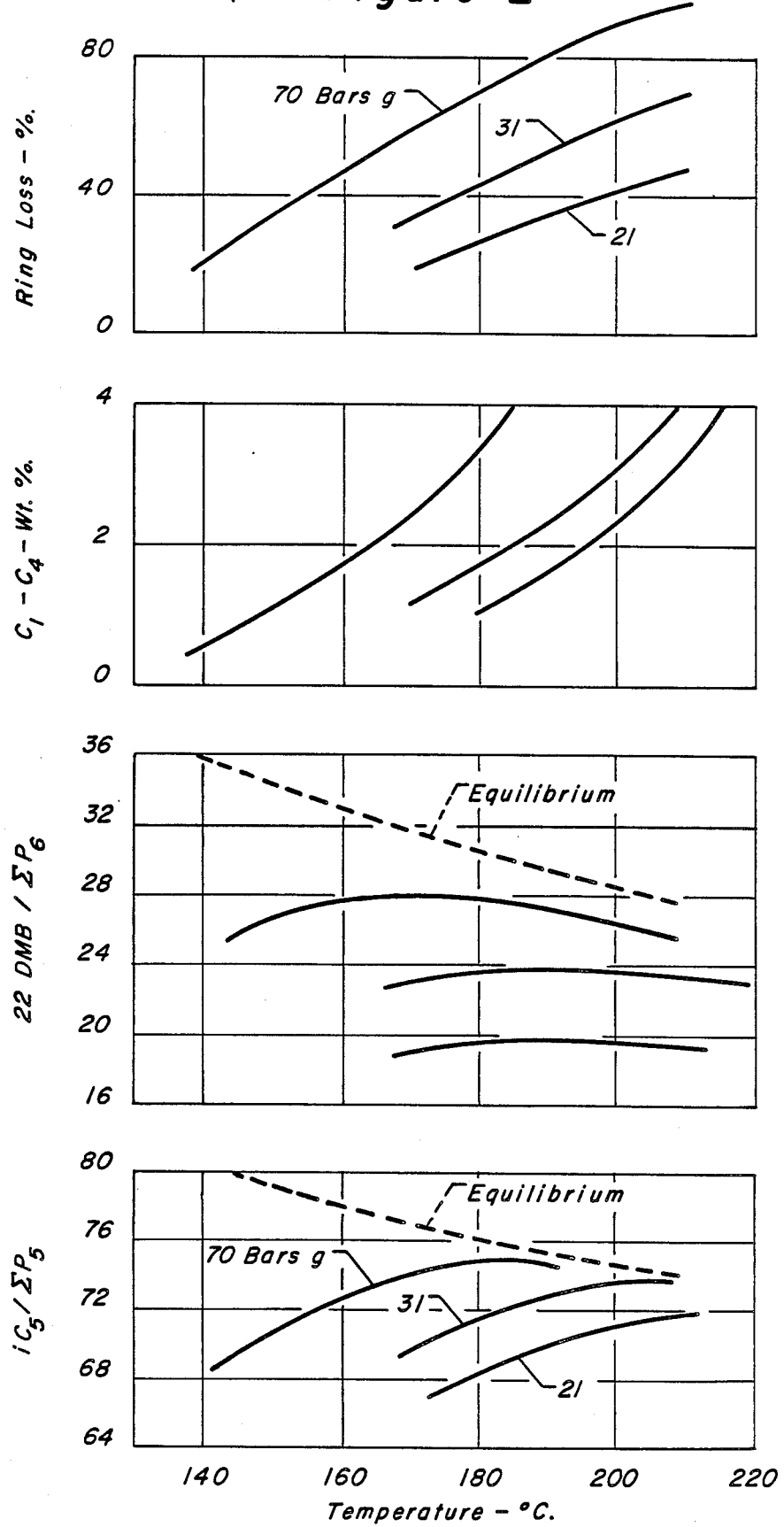

The synthetic feedstock of Example 1 was again passed through the reaction zone of Example 1 at a hydrogen to hydrocarbon molar ratio of 2 and a liquid hourly space velocity of 4. In substantially the same manner as carried out in Example 1, the temperature in reaction zone was varied periodically at pressure levels of 21, 31 and 70 barsg. The effluent from the reaction zone was monitored to provide data for the plots of FIG. 2 which show the ring opening percentage, $C_1$-$C_4$ hydrocarbon concentration, isopentane to $C_5$ hydrocarbon ratio and the 2,2-dimethylbutane to $C_6$ hydrocarbon ratio as a function of temperature. The plots shown in FIG. 1 again demonstrate the ability of the process to open rings while obtaining a good conversion of normal paraffins to isoparaffins without generating excess amounts of light hydrocarbons. Looking specifically at the plots for ring opening and $C_1$-$C_4$ hydrocarbon concentration, the overall effect of the higher space velocity is a rightward shifting of the performance profiles relative to FIG. 1 such that higher temperatures are required to obtain the percentage losses and conversions. The plots for isopentane and dimethylbutane conversion show a loss of conversion for Example 2 relative to Example 1.

EXAMPLES 3-5

In these examples, commercial feedstocks were contacted with the previously described catalyst. The feedstock passed through two reaction zones. The feed composition and the effluent properties after each reaction stage are listed in Tables 2 through 4 along with processing conditions for each reaction stage. In addition to verifying the ability of the process to open rings, achieve high conversion and not produce excessive light material, the data demonstrates that a majority of the ring opening occurs in the first stage. The data related to benzene also shows that any unsaturates that enter the process are rapidly hydrogenated.

EXAMPLE 6

Example 6 shows the operation of the process in the isomerization of $C_4$ hydrocarbons through a single reaction zone. In order to isomerize the $C_4$ hydrocarbons, the reaction zone operated at higher severity including an average reaction temperature at 220° C., a pressure of 31 barsg and a liquid hourly space velocity of 2 hr$^{-1}$. Throughout the test, a hydrogen to hydrocarbon molar ratio of 2 was maintained. The feed composition and effluent properties for this test appear in Table 5. Table 5 illustrates the effect higher severity has on increasing the percentage of ring opening.

TABLE 2

| | FEED | FIRST STAGE PRODUCT | SECOND STAGE PRODUCT |
|---|---|---|---|
| YIELDS wt. % | | | |
| $C_3$ | | 0.6 | 0.7 |
| I—$C_4$ | 0.1 | 1.8 | 2.3 |
| N—$C_4$ | 0.4 | 0.6 | 0.7 |
| $C_4$ Total | 0.5 | 2.4 | 3.0 |
| I—$C_5$ | 9.5 | 21.5 | 21.9 |
| N—$C_5$ | 18.4 | 7.5 | 7.1 |
| Cyclopentane | 2.9 | 2.3 | 2.0 |
| $C_5$ Total | 30.8 | 31.3 | 31.0 |
| 2,2-DMB | 3.2 | 14.9 | 17.2 |
| 2,3-DMB | 4.2 | 6.2 | 6.1 |
| 2-MP | 20.0 | 19.0 | 18.4 |
| 3-MP | 14.4 | 11.1 | 10.8 |
| MCP | 6.0 | 3.4 | 2.5 |
| N—Hexane | 16.9 | 7.6 | 7.4 |
| Cyclohexane | 0.9 | 2.2 | 1.7 |
| Benzene | 1.7 | 0.0 | 0.0 |
| $C_6$ Total | 67.3 | 64.4 | 64.0 |
| $C_7+$ Total | 1.4 | 1.3 | 1.3 |
| TOTAL | 100.0 | 100.0 | 100.0 |
| Reaction Conditions | | | |
| LHSV, hr.$^{-1}$ | | 2.0 | 2.0 |
| Ave. Rx Bed Temp., °C. | | 177 | 160 |
| ΔT | | 18.9 | 7.7 |
| Pressure Barsg | | | |
| Liquid Product Octanes | | | |
| RON-C | 69.8 | 81.7 | 82.2 |
| MON-C | 67.4 | 79.5 | 80.2 |
| Product Ratios | | | |
| i$C_5$/$C_5$P | 34.0 | 74.1 | 75.5 |
| 2,2-DMB/$C_6$P | 5.5 | 25.3 | 28.7 |
| 2,3-DMB/$C_6$P | 7.1 | 10.5 | 10.2 |
| % Ring Opening | | 35 | 51 |

TABLE 3

| | FEED | FIRST STAGE PRODUCT | SECOND STAGE PRODUCT |
|---|---|---|---|
| YIELDS wt. % | | | |
| $C_3$ | 0.1 | 0.4 | 0.4 |
| I—$C_4$ | 0.6 | 2.0 | 2.4 |
| N—$C_4$ | 1.1 | 1.1 | 1.1 |
| $C_4$ Total | 1.7 | 3.1 | 3.5 |
| I—$C_5$ | 16.0 | 28.2 | 29.5 |
| N—$C_5$ | 21.7 | 9.4 | 8.4 |
| Cyclopentane | 2.6 | 2.1 | 1.7 |
| $C_5$ Total | 40.3 | 39.7 | 39.6 |
| 2,2-DMB | 2.3 | 13.5 | 17.2 |
| 2,3-DMB | 2.8 | 5.0 | 5.0 |
| 2-MP | 15.4 | 15.0 | 14.5 |
| 3-MP | 9.4 | 8.6 | 8.0 |
| MCP | 5.3 | 4.1 | 2.7 |
| N—Hexane | 15.7 | 6.0 | 5.2 |
| Cyclohexane | 1.7 | 3.2 | 2.4 |
| Benzene | 3.7 | 0.0 | 0.0 |
| $C_6$ Total | 56.3 | 55.4 | 55.0 |
| $C_7+$ Total | 1.6 | 1.4 | 1.5 |
| TOTAL | 100.0 | 100.0 | 100.0 |
| Reaction Conditions | | | |
| LHSV, hr.$^{-1}$ | | 2.0 | 2.0 |
| Ave. Rx Bed Temp. | | 160 | 135 |
| ΔT | | 22.2 | 5.5 |
| Pressure Barsg | | | |

TABLE 3-continued

|  | FEED | FIRST STAGE PRODUCT | SECOND STAGE PRODUCT |
|---|---|---|---|
| Liquid Product Octanes | | | |
| RON-C | 70.9 | 82.3 | 83.3 |
| MON-C | 69.0 | 80.9 | 82.2 |
| Product Ratios | | | |
| iC$_5$/C$_5$P | 42.4 | 75.0 | 77.8 |
| 2,2-DMB/C$_6$P | 5.0 | 28.1 | 34.5 |
| 2,3-DMB/C$_6$P | 6.1 | 10.4 | 10.0 |
| % Ring Opening | | 32 | 52 |

TABLE 4

|  | FEED | FIRST STAGE PRODUCT | SECOND STAGE PRODUCT |
|---|---|---|---|
| YIELDS wt. % | | | |
| C$_3$ | 0.0 | 2.2 | 2.7 |
| I—C$_4$ | 0.2 | 4.7 | 5.4 |
| N—C$_4$ | 0.6 | 1.1 | 1.3 |
| C$_4$ Total | 0.8 | 5.8 | 6.7 |
| I—C$_5$ | 9.3 | 20.1 | 21.5 |
| N—C$_5$ | 18.1 | 7.6 | 6.8 |
| Cyclopentane | 2.5 | 2.1 | 1.9 |
| C$_5$ Total | 29.9 | 29.8 | 30.2 |
| 2,2-DMB | 2.7 | 11.2 | 13.9 |
| 2,3-DMB | 3.4 | 5.6 | 5.3 |
| 2-MP | 16.8 | 17.4 | 16.0 |
| 3-MP | 12.0 | 10.4 | 9.2 |
| MCP | 5.6 | 3.8 | 2.8 |
| N—Hexane | 15.4 | 7.3 | 6.8 |
| Cyclohexane | 1.4 | 2.2 | 2.4 |
| Benzene | 1.7 | 0.0 | 0.0 |
| C$_6$ Total | 59.0 | 57.9 | 56.3 |
| C$_7$+ Total | 10.3 | 4.3 | 4.1 |
| TOTAL | 100.0 | 100.0 | 100.0 |
| Reaction Conditions | | | |
| LHSV, hr.$^{-1}$ | | 2.0 | 2.0 |
| Ave. Rx Bed Temp., °C. | | 182 | 166 |
| ΔT | | 26.1 | 8.9 |
| Pressure Barsg | | | |
| Liquid Product Octanes | | | |
| RON-C | 70.3 | 82.7 | 83.8 |
| MON-C | 67.9 | 81.1 | 82.0 |
| Product Ratios | | | |
| iC$_5$/C$_5$P | 33.9 | 72.6 | 76.0 |
| 2,2-DMB/C$_6$P | 5.4 | 21.6 | 27.2 |
| 2,3-DMB/C$_6$P | 6.8 | 10.8 | 10.4 |
| % Ring Opening | | 31 | 41 |

TABLE 5

| Composition Wt. % | Feed | Product |
|---|---|---|
| C$_1$ | | 0.2 |
| C$_2$ | | 0.3 |
| C$_3$ | | 1.7 |
| IC$_4$ | | 18.5 |
| NC$_4$ | 33.6 | 16.7 |
| IC$_5$ | | 21.5 |
| N—C$_5$ | 26.7 | 7.7 |
| CP | 0.1 | 0.1 |
| 2,2 DMB | | 8.6 |
| 2,3 DMB | | 2.9 |
| 2-MP | | 10.6 |
| 3-MP | | 6.3 |
| N—C$_6$ | 32.0 | 4.5 |
| MCP | 2.6 | 0.2 |
| CH | 2.7 | 0.1 |
| Benzene | 2.3 | |
| C$_7$+ | | 0.1 |
| TOTAL | 100.0 | 100.0 |
| IC$_4$/C$_4$P | | 53 |
| IC$_5$/C$_5$P | | 74 |
| 22 DMB/C$_6$P | | 26 |

TABLE 5-continued

| Composition Wt. % | Feed | Product |
|---|---|---|
| Ring Opening, % | | 96 |

What is claimed is:

1. A process for the isomerization of a feedstream comprising C$_4$–C$_6$ isomerizable hydrocarbons and at least 2 wt.% cyclic hydrocarbons, said process comprising:

(a) passing said feedstream to a reaction zone and contacting said feedstream with a catalyst comprising alumina, from 0.1 to 0.25 wt.% platinum, and from 2 to 10 wt.% of a chloride component at isomerization conditions including a temperature in the range of from 20°–260° C. (105°–500° F.), a pressure of from 7 to 60 barsg and a liquid hourly space velocity of from 0.5 to 12;

(b) maintaining a chloride concentration of from 30 to 300 ppm, a sulfur concentration of less than 0.5 ppm, and an oxygenate concentration of less than 1 ppm in said reaction zone; and (c) recovering an effluent from said reaction zone having a weight percent concentration of cyclic hydrocarbons at least 40% lower than that of said feedstream.

2. The process of claim 1 wherein said reaction is carried out in at least two reaction zones and the first of said reaction zones is operated at a higher temperature.

3. The process of claim 1 wherein said feedstream comprises C$_5$–C$_6$ hydrocarbons and said isomerization conditions include a temperature in the range of from 120°–180° C. (250°–360° F.), a pressure in the range of 25 to 60 barsg and a space velocity of from 0.1 to 3.

4. The process of claim 3 wherein said isomerization conditions are selected to reduce the weight percent of cyclic hydrocarbons in said effluent by at least 80% and include a temperature of at least 160° C. (320° F.), a pressure of at least 45 barsg and a space velocity of less than 2.

5. A process for the isomerization of a feedstream comprising C$_4$–C$_6$ isomerizable hydrocarbons and including at least 2 wt.% cyclic hydrocarbons, said process comprising:

(a) passing said feedstream to a first reaction zone and contacting said feedstream with a first portion of a catalyst comprising alumina, from 0.1 to 0.25 wt.% platinum, and from 2 to 10 wt.% of a chloride component at isomerization conditions including a temperature in the range of from 100°–200° C. (160°–500° F.), a pressure of from 7 to 60 barsg and a space velocity of from 0.1 to 10;

(b) maintaining a chloride concentration of from 30 to 300 ppm, a sulfur concentration of less than 0.5 ppm, and an oxygenate concentrate of less than 0.1 ppm in said first reaction zone;

(c) recovering a first effluent stream from said first reaction zone having a reduced concentration of cyclic hydrocarbon relative to the feedstream;

(d) passing said first effluent stream to a second reaction zone and contacting said feedstream with a second portion of said catalyst at isomerization conditions including a temperature in the range of from 40°–200° C. (105°–390° F.), a pressure of from 7 to 60 barsg and a space velocity of from 0.1 to 10;

(e) maintaining a chloride concentration of from 30 to 300 ppm in, a sulfur concentration of less than 0.5 ppm, and an oxygenate concentrate of less than 0.1 ppm in said second reaction zone, and (f) recovering a second effluent stream from said second reaction zone having a weight percent concentration of cyclic hydrocarbons at least 40% lower than said feedstream.

6. The process of claim 5, wherein the space velocity in said reaction zones is less than 3, the pressure in said reaction zones is at least 30 barsg, the temperature in said first reaction zone is at least 180° C. (360° F.) and the temperature in said second reaction zone is less than 280° C. (360° F.).

* * * * *